(12) United States Patent
Zhao et al.

(10) Patent No.: US 11,504,698 B2
(45) Date of Patent: Nov. 22, 2022

(54) NI—$AL_2O_3$@$AL_2O_3$—$SIO_2$ CATALYST WITH COATED STRUCTURE, PREPARATION METHOD THEREFOR AND APPLICATION THEREOF

(71) Applicant: SHANXI UNIVERSITY, Shanxi (CN)

(72) Inventors: Yongxiang Zhao, Shanxi (CN); Haitao Li, Shanxi (CN); Lili Zhao, Shanxi (CN); Hongxi Zhang, Shanxi (CN); Zijin Sun, Shanxi (CN); Yongzhao Wang, Shanxi (CN)

(73) Assignee: SHANXI UNIVERSITY, Shanxi (CN)

( * ) Notice: Subject to any disclaimer, the term of this patent is extended or adjusted under 35 U.S.C. 154(b) by 675 days.

(21) Appl. No.: 16/483,369

(22) PCT Filed: Jan. 25, 2018

(86) PCT No.: PCT/CN2018/074144
§ 371 (c)(1),
(2) Date: Aug. 2, 2019

(87) PCT Pub. No.: WO2018/157685
PCT Pub. Date: Sep. 7, 2018

(65) Prior Publication Data
US 2020/0009538 A1  Jan. 9, 2020

(30) Foreign Application Priority Data

Feb. 28, 2017  (CN) .......................... 201710110022.7

(51) Int. Cl.
*B01J 23/755* (2006.01)
*B01J 23/00* (2006.01)
(Continued)

(52) U.S. Cl.
CPC ........... *B01J 23/755* (2013.01); *B01J 23/002* (2013.01); *B01J 35/0073* (2013.01);
(Continued)

(58) Field of Classification Search
CPC ............ B01J 21/12; B01J 21/04; B01J 21/08; B01J 23/755; B01J 23/002; B01J 35/0073;
(Continued)

(56) References Cited

U.S. PATENT DOCUMENTS 3,759,845 A * 9/1973 Rudoff .................. C07C 29/172
568/861
6,137,016 A 10/2000 Wood et al.
2003/0181327 A1 9/2003 Allison et al.

FOREIGN PATENT DOCUMENTS

CN  1453066  * 11/2003 ............ B01J 23/755
CN  1453066 A  11/2003
(Continued)

OTHER PUBLICATIONS

Chinese Search Report from Chinese Patent Application No. 201710110022.7, dated Dec. 5, 2018.
(Continued)

*Primary Examiner* — Patricia L. Hailey
(74) *Attorney, Agent, or Firm* — Greer, Burns & Crain, Ltd

(57) ABSTRACT

A Ni—$Al_2O_3$@$Al_2O_3$—$SiO_2$ catalyst with coated structure is provided. The catalyst has a specific surface area of 98 $m^2/g$ to 245 $m^2/g$, and a pore volume of 0.25 $cm^3/g$ to 1.1 $cm^3/g$. A mass ratio of an $Al_2O_3$ carrier to active component Ni in the catalyst is $Al_2O_3$:Ni=100:4~26, a mass ratio of the $Al_2O_3$ carrier to an $Al_2O_3$—$SiO_2$ coating layer is $Al_2O_3$:$Al_2O_3$—$SiO_2$=100:0.1~3, and a molar ratio of Al to Si in the $Al_2O_3$—$SiO_2$ coating layer is 0.01 to 1. Ni particles are distributed on a surface of the $Al_2O_3$ carrier in an amorphous or highly dispersed state and have a grain size less than or equal to 8 nm, and the coating layer is filled among the Ni particles.

19 Claims, 2 Drawing Sheets

(51) Int. Cl.
*B01J 35/00* (2006.01)
*B01J 35/10* (2006.01)
*B01J 37/02* (2006.01)
*B01J 37/06* (2006.01)
*B01J 37/16* (2006.01)
*C07C 29/141* (2006.01)
*C07C 29/17* (2006.01)
*C07C 31/20* (2006.01)

(52) U.S. Cl.
CPC ....... *B01J 35/1014* (2013.01); *B01J 35/1019* (2013.01); *B01J 35/1038* (2013.01); *B01J 35/1042* (2013.01); *B01J 37/0213* (2013.01); *B01J 37/06* (2013.01); *B01J 37/16* (2013.01); *C07C 29/141* (2013.01); *C07C 29/172* (2013.01); *C07C 31/207* (2013.01)

(58) Field of Classification Search
CPC ................ B01J 37/1014; B01J 35/1019; B01J 35/1038; B01J 35/1042; B01J 37/0213; B01J 37/06; B01J 37/16; C07C 29/141; C07C 29/172; C07C 31/207
USPC .................................................. 502/259, 337
See application file for complete search history.

(56) References Cited

FOREIGN PATENT DOCUMENTS

| | | | | | |
|---|---|---|---|---|---|
| CN | 101322949 | A | | 12/2008 | |
| CN | 101502802 | A | | 8/2009 | |
| CN | 102145286 | | * | 8/2011 | |
| CN | 102145286 | A | | 8/2011 | |
| CN | 106902825 | A | | 6/2017 | |
| CN | 106902826 | | * | 6/2017 | .......... B01J 35/1042 |
| CN | 106902826 | A | | 6/2017 | |
| EP | 0319116 | A1 | * | 6/1989 | .............. B01J 23/89 |
| WO | WO-2018177709 | A1 | * | 10/2018 | .............. B01J 23/40 |

OTHER PUBLICATIONS

International Search Report from International Patent Application No. PCT/CN2018/074144, dated May 2, 2018.
Li et al., "Study on Deactivation of Ni/Al2O3 Catalyst for Liquid Phase Hydrogenation of Crude 1,4-Butanediol Aqueous Solution", Chemical Engineering Journal (2012), vols. 181-182, pp. 501-507.

* cited by examiner

NI—AL$_2$O$_3$@AL$_2$O$_3$—SIO$_2$ CATALYST WITH COATED STRUCTURE, PREPARATION METHOD THEREFOR AND APPLICATION THEREOF

BACKGROUND

1. Field of the Invention

The invention relates to a Ni—Al$_2$O$_3$@Al$_2$O$_3$—SiO$_2$ catalyst with coated structure, a preparation method thereof and an application thereof.

2. Related Art

Cyclic acetal, 2-(4'-hydroxybutoxy)-tetrahydrofuran is an unavoidable by-product during hydrogenation of 1,4-butynediol to prepare butane-1,4-diol using a Reppe process. The cyclic acetal, 2-(4'-hydroxybutoxy)-tetrahydrofuran itself cannot be removed by direct hydrogenation, and because it forms an azeotrope with butane-1,4-diol, it is difficult to separate it using conventional distillation method. Remaining of acetal, 2-(4'-hydroxybutoxy)-tetrahydrofuran seriously affects purity and chromaticity of butane-1,4-diol products, and directly affects quality of butane-1,4-diol and its application in the downstream field.

U.S. Pat. No. 6,137,016 describes a process for the purification of butane-1,4-diol containing a minor amount of cyclic acetal, 2-(4'-hydroxybutoxy)-tetrahydrofuran by hydrogenation, and since the hydrogenation catalyst used therein is a general-purpose hydrogenation catalyst, the hydrogenation effect is not ideal. CN 102145286 B discloses a Ni—SiO$_2$/Al$_2$O$_3$ catalyst and a preparation method thereof, wherein the catalyst can effectively realize hydrolyzation and hydrogenation conversion of cyclic acetal, 2-(4'-hydroxybutoxy)-tetrahydrofuran, but the preparation process is complicated.

SUMMARY

An object of the invention is to provide a Ni—Al$_2$O$_3$@Al$_2$O$_3$—SiO$_2$ catalyst with coated structure which is easy to prepare and has good selectivity, a preparation method thereof and an application thereof.

In order to achieve the above object, the invention provides a Ni—Al$_2$O$_3$@Al$_2$O$_3$—SiO$_2$ catalyst with coated structure, characterized in that Ni particles are distributed on a surface of an Al$_2$O$_3$ carrier in an amorphous or highly dispersed state as an active component for the catalyst and have a grain size less than or equal to 8 nm, a mass ratio of the Al$_2$O$_3$ carrier to an Al$_2$O$_3$—SiO$_2$ coating layer is Al$_2$O$_3$:Al$_2$O$_3$—SiO$_2$=100:0.1~3, a molar ratio of Al to Si in the Al$_2$O$_3$—SiO$_2$ coating layer is 0.01~0.1:1, and the coating layer is filled among the Ni particles.

Regarding the Ni—Al$_2$O$_3$@Al$_2$O$_3$—SiO$_2$ catalyst with coated structure according to the invention, the catalyst has a specific surface area preferably 98 m$^2$/g to 245 m$^2$/g, and a pore volume preferably 0.25 cm$^3$/g to 1.1 cm$^3$/g, and a mass ratio of the Al$_2$O$_3$ carrier to the active component Ni in the catalyst is preferably Al$_2$O$_3$:Ni=100:4~26.

In order to achieve the above object, the invention further provides a preparation method of the Ni—Al$_2$O$_3$@Al$_2$O$_3$—SiO$_2$ catalyst with coated structure, comprising the steps of:

impregnation step: loading the active component Ni onto the Al$_2$O$_3$ carrier using an impregnation method, Ni being distributed in tetrahedral and octahedral holes on an Al$_2$O$_3$ surface and growing into microcrystalline particles by using the tetrahedral and octahedral holes as nuclei;

deposition step: loading the Al$_2$O$_3$—SiO$_2$ layer in a depositing manner onto a surface of a Ni/Al$_2$O$_3$ catalyst obtained in the impregnation step, Al$_2$O$_3$—SiO$_2$ only deposited on the Al$_2$O$_3$ surface exposed in gaps of the Ni particles; and washing step: removing weak adsorption compositions remaining on the surface of the catalyst by washing the deposited sample.

In order to achieve the above object, the invention further provides another preparation method of the Ni—Al$_2$O$_3$@Al$_2$O$_3$—SiO$_2$ catalyst with coated structure, comprising the steps of:

(1) cooling the Al$_2$O$_3$ carrier to a room temperature for use after treatment at 100° C. to 150° C.;

(2) preparing a nickel salt water solution having a nickel content of 0.05 g/mL to 0.2 g/mL;

(3) impregnating the nickel salt water solution prepared by step (2) into the carrier of step (1) according to a ratio of 80 mL to 130 mL of nickel salt solution for 100 g of the Al$_2$O$_3$ carrier, standing, drying and calcining to obtain a NiO/Al$_2$O$_3$ precursor;

(4) preparing an ethanol-water solution of aluminum precursor and silicon precursor with a total concentration of 0.0001 g/mL to 0.0015 g/mL by calculating Al$_2$O$_3$ and SiO$_2$, and adjusting a pH value of the ethanol-water solution to 8.0 to 8.5 by ammonia water, wherein a molar ratio of Al to Si is 0.01~0.1:1;

(5) suspending the NiO/Al$_2$O$_3$ precursor obtained by step (3) in the solution prepared by step (4) according to an amount of 1000 mL to 2000 mL of ethanol-water solution of aluminum precursor and silicon precursor for 100 g of Al$_2$O$_3$ in the NiO/Al$_2$O$_3$ precursor of step (3), stirring and refluxing at a constant temperature, centrifugal washing respectively with absolute ethyl alcohol, dilute nitric acid and deionized water after filtration, and drying;

(6) calcining the sample obtained by step (5), then conducting hydrogen reduction to obtain a Ni—Al$_2$O$_3$@Al$_2$O$_3$—SiO$_2$ catalyst.

In order to achieve the above object, the invention further provides another preparation method of the Ni—Al$_2$O$_3$@Al$_2$O$_3$—SiO$_2$ catalyst with coated structure, comprising the steps of:

(1) vacuum treating the Al$_2$O$_3$ carrier for 10 mins to 30 mins at 100° C. to 150° C., or directly heating for 1 hour to 10 hours at 100° C. to 150° C., and then cooling to a room temperature for use;

(2) preparing a nickel salt solution having a nickel content of 0.05 g/mL to 0.2 g/mL;

(3) impregnating the nickel salt solution prepared by step (2) into the carrier of step (1) according to a ratio of 80 mL to 130 mL of nickel salt solution for 100 g of the Al$_2$O$_3$ carrier, standing for 20 mins to 120 mins, then drying for 2 hours to 24 hours at a temperature raised to 100° C. to 150° C., and calcining for 1 hour to 24 hours at a constant temperature of 350° C. to 500° C. raised at 2° C./min to 10° C./min in an air or nitrogen atmosphere to obtain a NiO/Al$_2$O$_3$ precursor;

(4) preparing an ethanol-water solution of aluminum precursor and silicon precursor with a total concentration of 0.0001 g/mL to 0.0015 g/mL by calculating Al$_2$O$_3$ and SiO$_2$, and adjusting a pH value of the ethanol-water solution to 8.0 to 8.5 by ammonia water, wherein a molar ratio of Al to Si is 0.01~0.1:1;

(5) suspending the NiO/Al$_2$O$_3$ precursor obtained by step (3) in the solution prepared by step (4) according to an amount of 1000 mL to 2000 mL of ethanol-water solution of aluminum precursor and silicon precursor for 100 g of the $Al_2O_3$ carrier in the $NiO/Al_2O_3$ precursor of step (3), stirring and refluxing for 1 hour to 24 hours at a constant temperature of 20° C. to 60° C., centrifugal washing three to five times respectively with absolute ethyl alcohol, 0.01M dilute nitric acid and deionized water after filtration, and drying the sample for 2 hours to 24 hours at 80° C. to 150° C.;

(6) calcining the sample obtained by step (5) for 1 hour to 24 hours at a constant temperature of 400° C. to 550° C. raised at 2° C./min to 10° C./min in an air or nitrogen atmosphere, and then conducting reduction for 1 hour to 24 hours at 350° C. to 650° C. under the condition of a gas space velocity (GSV) of hydrogen of 500/h to 2000/h to obtain a $Ni$—$Al_2O_3$@$Al_2O_3$—$SiO_2$ catalyst.

Regarding the preparation method of the $Ni$—$Al_2O_3$@$Al_2O_3$—$SiO_2$ catalyst with coated structure according to the invention, the $Al_2O_3$ carrier in step (1) has a specific surface area preferably 110 $m^2/g$ to 260 $m^2/g$, and a pore volume preferably 0.5 $cm^3/g$ to 1.3 $cm^3/g$.

Regarding the preparation method of the $Ni$—$Al_2O_3$@$Al_2O_3$—$SiO_2$ catalyst with coated structure according to the invention, the nickel salt in the nickel salt water solution of step (2) is preferably one of a nickel nitrate, a nickel sulfate or a nickel chloride.

Regarding the preparation method of the $Ni$—$Al_2O_3$@$Al_2O_3$—$SiO_2$ catalyst with coated structure according to the invention, a drying time in step (3) is 3 hours to 12 hours.

Regarding the preparation method of the $Ni$—$Al_2O_3$@$Al_2O_3$—$SiO_2$ catalyst with coated structure according to the invention, the silicon precursor in step (3) is preferably one of tetraethoxysilane (TEOS), or tetramethoxysilane (TMOS).

Regarding the preparation method of the $Ni$—$Al_2O_3$@$Al_2O_3$—$SiO_2$ catalyst with coated structure according to the invention, the silicon precursor is further preferably TEOS.

Regarding the preparation method of the $Ni$—$Al_2O_3$@$Al_2O_3$—$SiO_2$ catalyst with coated structure according to the invention, the aluminum precursor in step (3) is preferably one of aluminum isopropoxide, aluminum n-butanol, or aluminum nitrate.

Regarding the preparation method of the $Ni$—$Al_2O_3$@$Al_2O_3$—$SiO_2$ catalyst with coated structure according to the invention, the aluminum precursor is further preferably aluminum nitrate.

Regarding the preparation method of the $Ni$—$Al_2O_3$@$Al_2O_3$—$SiO_2$ catalyst with coated structure according to the invention, a molar ratio of ethanol to water in the ethanol-water solution of step (3) is preferably 4~100:1.

Regarding the preparation method of the $Ni$—$Al_2O_3$@$Al_2O_3$—$SiO_2$ catalyst with coated structure according to the invention, a drying time in step (5) is preferably 3 hours to 12 hours.

In order to achieve the above object, the invention further provides an application of the $Ni$—$Al_2O_3$@$Al_2O_3$—$SiO_2$ catalyst with coated structure, wherein the catalyst is for hydrogenation of 1,4-butynediol to catalytic synthesize butane-1,4-diol.

Regarding the application of the $Ni$—$Al_2O_3$@$Al_2O_3$—$SiO_2$ catalyst with coated structure according to the invention, preferably, it comprises the following step A:

the catalyst for hydrogenation of 1,4-butynediol under a high pressure to catalytic synthesize butane-1,4-diol, wherein a raw material contains 64 wt % to 72 wt % water, an organic phase contains 90 wt % to 91.5 wt % butane-1,4-diol, 1 wt % to 2 wt % butanol, 1.3 wt % to 1.8 wt % 4-hydroxybutyraldehyde, 1.5 wt % to 2 wt % 1,4-butynediol, 2.7 wt % to 3.2 wt % 1,4-butenediol, and 0.8 wt % to 1.2 wt % cyclic acetal, 2-(4'-hydroxybutoxy)-tetrahydrofuran, the carbonyl number is 8 mg(KOH)/g to 12 mg(KOH)/g, and hydrogenation is conducted under the conditions of a reaction temperature of 100° C. to 150° C., a $H_2$ pressure of 10 MPa to 20 MPa, and a liquid hourly space velocity (LHSV) of 1.1/h to 1.7/h.

Regarding the application of the $Ni$—$Al_2O_3$@$Al_2O_3$—$SiO_2$ catalyst with coated structure according to the invention, an organic phase product after hydrogenation of step A contains 96.44 wt % to 97.76 wt % butane-1,4-diol, 1.3 wt % to 2.5 wt % butanol, 0.03 wt % to 0.08 wt % 4-hydroxybutyraldehyde, 0.01 wt % to 0.05 wt % 1,4-butynediol, 0.03 wt % to 0.07 wt % 1,4-butenediol, and 0.01 wt % to 0.03 wt % cyclic acetal, 2-(4'-hydroxybutoxy)-tetrahydrofuran, and the carbonyl number is 0.03 mg(KOH)/g to 0.05 mg(KOH)/g.

Regarding the application of the $Ni$—$Al_2O_3$@$Al_2O_3$—$SiO_2$ catalyst with coated structure according to the invention, preferably, it comprises the following step B:

the catalyst for direct hydrogenation conversion of a raw material which is a water solution containing 25 wt % to 35 wt % 1,4-butynediol using an external cyclic hydrogenation process, wherein the way of feeding is up-in and down-out., and reaction conditions are a reaction temperature of 105° C. to 150° C., a hydrogen pressure of 10 MPa to 22 MPa, an liquid hourly space velocity (LHSV) of 1.0/h to 1.7/h, and a recycle ratio of 22:1.

Regarding the application of the $Ni$—$Al_2O_3$@$Al_2O_3$—$SiO_2$ catalyst with coated structure according to the invention, an organic phase of the material after hydrogenation of step B contains butane-1,4-diol greater than or equal to 96 wt %, by-product butanol less than or equal to 1.2 wt %, and a total unsaturated chromogenic substance less than or equal to 0.06 wt %, the remaining is macromolecular polymer, and the carbonyl number of the material is 0.03 mg(KOH)/g to 0.05 mg(KOH)/g.

As compared to the prior arts, the invention has the following advantages:

1. The active component Ni is loaded onto the $Al_2O_3$ carrier using an impregnation method, Ni being distributed in tetrahedral and octahedral holes on an $Al_2O_3$ surface, which are used as nuclei to grow into microcrystalline particles. The particles have a high dispersity.

2. The $Al_2O_3$—$SiO_2$ layer is loaded in a depositing manner onto a surface of a $Ni/Al_2O_3$ catalyst, and since $SiO_2$ does not react with NiO, and interaction there between is extremely weak, $Al_2O_3$—$SiO_2$ is only deposited on the $Al_2O_3$ surface exposed in gaps of the NiO particles. With increasing of the content of $Al_2O_3$—$SiO_2$, when the exposed $Al_2O_3$ surface is fully covered by a single layer of $Al_2O_3$—$SiO_2$, two, three, four . . . layers of $Al_2O_3$—$SiO_2$ are further grown on the surface of the exposed single layer $Al_2O_3$—$SiO_2$.

3. Weak adsorption compositions remaining on the surface of the catalyst during grafting process, in particular, the $Al_2O_3$—$SiO_2$ layer weakly adsorbed on the NiO surface, is effectively removed by washing a deposited sample with absolute ethyl alcohol, 0.01M dilute nitric acid and deionized water, which ensures effective exposure of the active component Ni particles.

4. During preparation of the traditional catalyst, due to strong interaction between NiO and $Al_2O_3$, reduction of NiO to the active component Ni is often conducted in a high temperature, while high reduction temperature promotes migration and aggregation of the metal Ni, reduces the number of surface active sites, and also correspondingly reduces hydrogenation activity. In the invention, the $Al_2O_3$—$SiO_2$ layer is disposed between gaps of the NiO particles, and migration and aggregation of the metal Ni during the high temperature reduction can be effectively prevented by a confinement effect, so that the active metal nickel remains a high dispersity, and the catalyst exhibits a high hydrogenation activity.

5. The Al—O—Si structure formed by the $Al_2O_3$—$SiO_2$ layer enables it to have a specific surface acidic property, which facilitates hydrolyzation of cyclic acetal, 2-(4'-hydroxybutoxy)-tetrahydrofuran to 4-hydroxybutyraldehyde, and then hydrogenation conversion to butane-1,4-diol under catalysis of adjacent high activity exposed hydrogenation center Ni. Synergistic effect of the acidic center and the hydrogenation active center in the catalyst achieves efficient conversion of cyclic acetal, 2-(4'-hydroxybutoxy)-tetrahydrofuran, and finally reaches objects of reducing the content of cyclic acetal, 2-(4'-hydroxybutoxy)-tetrahydrofuran, improving product quality of butane-1,4-diol, and reducing product chromaticity.

6. The $Al_2O_3$—$SiO_2$ layer is coated on the $Al_2O_3$ surface, which prevents attack of water to the $Al_2O_3$ carrier, inhibits hydration destruction of the $Al_2O_3$ carrier, effectively improves hydrothermal stability of the catalyst in a water containing system, and prolongs service life of the catalyst.

DETAILED DESCRIPTION

Figure 1:
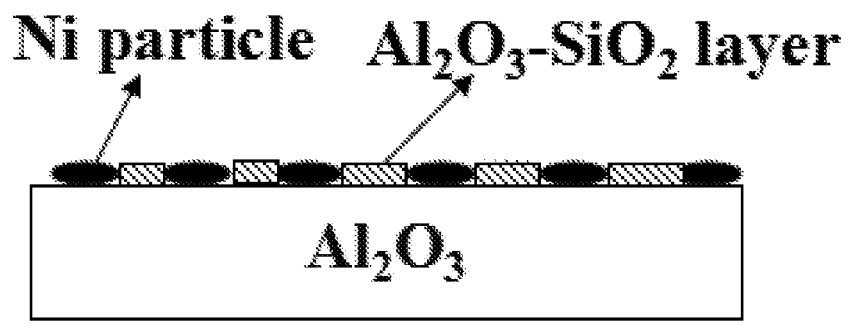
FIG. 1 is a structure diagram of the Ni—$Al_2O_3$@$Al_2O_3$—$SiO_2$ catalyst according to the invention.

Hereinafter examples of the invention are explained in detail: the examples are carried out on the premise of the technical solution of the invention with detailed embodiments and processes, but the extent of protection of the invention is not limited to the examples below. Generally, experimental method without indicating specific conditions in the examples follows conventional conditions.

The catalyst of the invention has a specific surface area of 98 $m^2$/g to 245 $m^2$/g, and a pore volume of 0.25 $cm^3$/g to 1.1 $cm^3$/g, and a mass ratio of an $Al_2O_3$ carrier to the active component Ni in the catalyst is $Al_2O_3$:Ni=100:4~26. Ni particles are distributed on a surface of the $Al_2O_3$ carrier in an amorphous or highly dispersed state and have a grain size less than 8 nm, a mass ratio of the $Al_2O_3$ carrier to an $Al_2O_3$—$SiO_2$ coating layer is $Al_2O_3$:$Al_2O_3$—$SiO_2$=100: 0.1~3, a molar ratio of Al to Si in the $Al_2O_3$—$SiO_2$ coating layer is 0.01~0.1:1, and the coating layer is filled among the Ni particles.

A preparation method of the Ni—$Al_2O_3$@$Al_2O_3$—$SiO_2$ catalyst with coated structure provided in the invention comprises steps of:

(1) vacuum treating the $Al_2O_3$ carrier for 10 mins to 30 mins at 100° C. to 150° C., or directly heating for 1 hour to 10 hours at 100° C. to 150° C., and then cooling to a room temperature for use;

(2) preparing a nickel salt solution having a nickel content of 0.05 g/mL to 0.2 g/mL;

(3) impregnating the nickel salt solution prepared by step (2) into the carrier of step (1) according to a ratio of 80 mL to 130 mL of nickel salt solution for 100 g of the $Al_2O_3$ carrier, standing for 20 mins to 120 mins, then drying for 2 hours to 24 hours, preferably 3 hours to 12 hours, at a temperature raised to 100° C. to 150° C., and calcining for 1 hour to 24 hours at a constant temperature of 350° C. to 500° C. raised at 2° C./min to 10° C./min in an air or nitrogen atmosphere to obtain a NiO/$Al_2O_3$ precursor;

(4) preparing an ethanol-water solution of aluminum precursor and silicon precursor with a total concentration of 0.0001 g/mL to 0.0015 g/mL by calculating $Al_2O_3$ and $SiO_2$ in the solution, and adjusting a pH value of the ethanol-water solution to 8.0 to 8.5 by ammonia water;

(5) suspending the NiO/$Al_2O_3$ precursor obtained by step (3) in the solution prepared by step (4) according to an amount of 1000 mL to 2000 mL of ethanol-water solution of aluminum precursor and silicon precursor for 100 g of $Al_2O_3$ in the NiO/$Al_2O_3$ precursor of step (3), stirring and refluxing for 1 hour to 24 hours at a constant temperature of 20° C. to 60° C., centrifugal washing three to five times respectively with absolute ethyl alcohol, 0.01M dilute nitric acid and deionized water after filtration, and drying the sample for 2 hours to 24 hours, preferably 3 hours to 12 hours, at 80° C. to 150° C.;

(6) calcining the sample obtained by step (5) for 1 hour to 24 hours at a constant temperature of 400° C. to 550° C. raised at 2° C./min to 10° C./min in an air or nitrogen atmosphere, and then conducting reduction for 1 hour to 24 hours at 350° C. to 650° C. under the condition of a gas space velocity of hydrogen of 500/h to 2000/h to obtain a Ni—$Al_2O_3$@$Al_2O_3$—$SiO_2$ catalyst.

The $Al_2O_3$ in step (1) has a specific surface area of 110 $m^2$/g to 260 $m^2$/g, and a pore volume of 0.5 $cm^3$/g to 1.3 $cm^3$/g.

The nickel salt in step (2) is selected from one of a nickel nitrate, a nickel sulfate or a nickel chloride.

The silicon precursor in step (4) is one of tetraethoxysilane (TEOS), or tetramethoxysilane (TMOS), preferably TEOS, the aluminum precursor is one of aluminum isopropoxide, aluminum n-butanol, or aluminum nitrate, preferably aluminum nitrate, and a molar ratio of ethanol to water in the ethanol-water solution is 4~100:1.

An application of the catalyst in the invention comprises step of:

the catalyst for hydrogenation of 1,4-butynediol under a high pressure to catalytic synthesize butane-1,4-diol, wherein a raw material contains 64 wt % to 72 wt % water, an organic phase contains 90 wt % to 91.5 wt % butane-1, 4-diol, 1 wt % to 2 wt % butanol, 1.3 wt % to 1.8 wt % 4-hydroxybutyraldehyde, 1.5 wt % to 2 wt % 1,4-butynediol, 2.7 wt % to 3.2 wt % 1,4-butenediol, and 0.8 wt % to 1.2 wt % cyclic acetal, 2-(4'-hydroxybutoxy)-tetrahydrofuran, the carbonyl number is 8 mg(KOH)/g to 12 mg(KOH)/g, and hydrogenation is conducted under the conditions of a reaction temperature of 100° C. to 150° C., a pressure of 10 MPa to 20 MPa, and a liquid hourly space velocity of 1.1/h to 1.7/h. The organic phase after hydrogenation contains 96.44 wt % to 97.76 wt % butane-1,4-diol, 1.3 wt % to 2.5 wt % butanol, 0.03 wt % to 0.08 wt % 4-hydroxybutyraldehyde, 0.01 wt % to 0.05 wt % 1,4-butynediol, 0.03 wt % to 0.07 wt % 1,4-butenediol, and 0.01 wt % to 0.03 wt % cyclic acetal, 2-(4'-hydroxybutoxy)-tetrahydrofuran, and the carbonyl number is 0.03 mg(KOH)/g to 0.05 mg(KOH)/g.

The catalyst is also suitable for direct hydrogenation conversion of a raw material which is a water solution containing 25 wt % to 35 wt % 1,4-butynediol using an external cyclic hydrogenation process, wherein a way of feeding is up-in and down-out, and reaction conditions are a reaction temperature of 105° C. to 150° C., a hydrogen pressure of 10 MPa to 22 MPa, a liquid hourly space velocity of 1.0/h to 1.7/h, and a recycle ratio of 18~22:1. The organic phase of the material after hydrogenation contains butane-1,4-diol greater than or equal to 96 wt %, by-product butanol less than or equal to 1.2 wt %, and a total unsaturated chromogenic substance of 1,4-butynediol, 1,4-butenediol, 4-hydroxybutyraldehyde, hemiacetal and acetal, 2-(4'-hydroxybutoxy)-tetrahydrofuran less than or equal to 0.06 wt %, the remaining is macromolecular polymer, and the carbonyl number of the material is 0.03 mg(KOH)/g to 0.05 mg(KOH)/g.

EXAMPLE 1

(1) The $Al_2O_3$ carrier having a specific surface area of 110 $m^2/g$, and a pore volume of 0.5 $cm^3/g$ was vacuum treated for 10 mins at 100° C., and then cooled to a room temperature for use; a nickel nitrate solution having a nickel content of 0.05 g/mL was prepared; 80 mL of the prepared nickel salt solution was impregnated into 100 g of the $Al_2O_3$ carrier, stood for 20 mins, then dried for 2 hours at a temperature raised to 100° C., and calcined for 1 hour at a constant temperature of 350° C. raised at 2° C./min in an air atmosphere to obtain a $NiO/Al_2O_3$ precursor having a mass ratio of $Al_2O_3$:Ni to be 100:4.

The ethanol-water solution of aluminum precursor and silicon precursor with a concentration of 0.0001 g/mL by calculating $Al_2O_3$—$SiO_2$ was prepared from aluminum isopropoxide and TEOS with a molar ratio of Al:Si to be 0.01:1, a molar ratio of ethanol to water in the ethanol-water solution was 4:1, and a pH value of the ethanol-water solution was adjusted to be 8.0 by ammonia water. The $NiO/Al_2O_3$ precursor prepared with the mass ratio of $Al_2O_3$:Ni to be 100:4 was suspended in 1000 mL of ethanol-water solution of aluminum precursor and silicon precursor, stirred and refluxed for 1 h at a constant temperature of 20° C., centrifugal washed three times respectively with absolute ethyl alcohol, 0.01M dilute nitric acid and deionized water after filtration, and the sample was dried for 2 hours at 80° C. The obtained sample was placed in a muffle furnace to calcine for 1 hour at a constant temperature of 400° C. raised at 2° C./min in an air atmosphere, and then reduction was conducted for 1 hour at 350° C. under the condition of a gas space velocity (GSV) of hydrogen of 500/h to obtain a Ni—$Al_2O_3$@$Al_2O_3$—$SiO_2$ catalyst with a quality composition of $Al_2O_3$:$Al_2O_3$—$SiO_2$:Ni=100:0.1:4, wherein a molar ratio of Al:Si in the $Al_2O_3$—$SiO_2$ layer was 0.01:1. The catalyst had a specific surface area of 105 $m^2/g$, and a pore volume of 0.45 $cm^3/g$, Ni particles were being in an amorphous state, and the $Al_2O_3$—$SiO_2$ layer formed Al—O—Si bonds that filled among the Ni particles. The catalyst was numbered as 1 #.

EXAMPLE 2

(1) The $Al_2O_3$ carrier having a specific surface area of 110 $m^2/g$, and a pore volume of 0.5 $cm^3/g$ was vacuum treated for 30 mins at 150° C., and then cooled to a room temperature for use; a nickel salt solution of nickel sulfate having a nickel content of 0.2 g/mL was prepared; 130 mL of the prepared nickel salt solution was impregnated into 100 g of the $Al_2O_3$ carrier, stood for 120 mins, then dried for 24 hours at a temperature raised to 150° C., and calcined for 24 hours at a constant temperature of 500° C. raised at 10° C./min in a nitrogen atmosphere to obtain a $NiO/Al_2O_3$ precursor having a mass ratio of $Al_2O_3$:Ni to be 100:26.

The ethanol-water solution of aluminum precursor and silicon precursor with a concentration of 0.0015 g/mL by calculating $Al_2O_3$—$SiO_2$ was prepared from aluminum n-butanol and TMOS with a molar ratio of Al:Si to be 0.08:1, a molar ratio of ethanol to water in the ethanol-water solution was 100:1, and a pH value of the ethanol-water solution was adjusted to be 8.5 by ammonia water. The $NiO/Al_2O_3$ precursor prepared with the mass ratio of $Al_2O_3$:Ni to be 100:26 was suspended in 2000 mL of ethanol-water solution of aluminum precursor and silicon precursor, stirred and refluxed for 24 hours at a constant temperature of 60° C., centrifugal washed five times respectively with absolute ethyl alcohol, 0.01M dilute nitric acid and deionized water after filtration, and the sample was dried for 24 hours at 150° C. The obtained sample was placed in a muffle furnace to calcine for 24 hours at a constant temperature of 550° C. raised at 10° C./min in a nitrogen atmosphere, and then reduction was conducted for 24 hours at 650° C. under the condition of a gas space velocity of hydrogen of 2000/h to obtain a Ni—$Al_2O_3$@$Al_2O_3$—$SiO_2$ catalyst with a quality composition of $Al_2O_3$:$Al_2O_3$—$SiO_2$:Ni=100:3:26, wherein a molar ratio of Al:Si in the $Al_2O_3$—$SiO_2$ layer was 0.08:1. The catalyst had a specific surface area of 98 $m^2/g$, and a pore volume of 0.25 $cm^3/g$, Ni particles were distributed on a surface of the $Al_2O_3$ carrier in a highly dispersed state and had a grain size of 8 nm, and the $Al_2O_3$—$SiO_2$ layer formed Al—O—Si bonds that filled among the Ni particles. The catalyst was numbered as 2 #.

EXAMPLE 3

(1) The $Al_2O_3$ carrier having a specific surface area of 260 $m^2/g$, and a pore volume of 1.3 $cm^3/g$ was heated for 1 hour at 100° C. in an air-circulating oven, and then cooled to a room temperature for use; a nickel salt solution of nickel chloride having a nickel content of 0.05 g/mL was prepared; 80 mL of the prepared nickel salt solution was impregnated into 100 g of the $Al_2O_3$ carrier, stood for 80 mins, then dried for 3 hours at a temperature raised to 120° C., and calcined for 18 hours at a constant temperature of 450° C. raised at 8° C./min in an air atmosphere to obtain a $NiO/Al_2O_3$ precursor having a mass ratio of $Al_2O_3$:Ni to be 100:4.

The ethanol-water solution of aluminum precursor and silicon precursor with a concentration of 0.0001 g/mL by calculating $Al_2O_3$—$SiO_2$ was prepared from aluminum nitrate and TMOS with a molar ratio of Al:Si to be 0.1:1, a molar ratio of ethanol to water in the ethanol-water solution was 10:1, and a pH value of the ethanol-water solution was adjusted to be 8.2 by ammonia water. The $NiO/Al_2O_3$ precursor prepared with the mass ratio of $Al_2O_3$:Ni to be 100:4 was suspended in 1000 mL of ethanol-water solution of aluminum precursor and silicon precursor, stirred and refluxed for 12 hours at a constant temperature of 40° C., centrifugal washed four times respectively with absolute ethyl alcohol, 0.01M dilute nitric acid and deionized water after filtration, and the sample was dried for 3 hours at 150° C. The obtained sample was placed in a muffle furnace to calcine for 12 hours at a constant temperature of 500° C. raised at 8° C./min in a nitrogen atmosphere, and then reduction was conducted for 10 hours at 550° C. under the condition of a gas space velocity of hydrogen of 1000/h to obtain a Ni—$Al_2O_3$@$Al_2O_3$—$SiO_2$ catalyst with a quality composition of $Al_2O_3$:$Al_2O_3$—$SiO_2$:Ni=100:0.1:4, wherein a molar ratio of Al:Si in the $Al_2O_3$—$SiO_2$ layer was 0.1:1.

The catalyst had a specific surface area of 245 m²/g, and a pore volume of 1.10 cm³/g, Ni particles were distributed on a surface of the $Al_2O_3$ carrier in an amorphous state, and the $Al_2O_3$—$SiO_2$ layer formed Al—O—Si bonds that filled among the Ni particles. The catalyst was numbered as 3 #.

EXAMPLE 4

(1) The $Al_2O_3$ carrier having a specific surface area of 160 m²/g, and a pore volume of 0.75 cm³/g was heated for 10 hours at 150° C. in an air-circulating oven, and then cooled to a room temperature for use; a nickel salt solution of nickel nitrate having a nickel content of 0.10 g/mL was prepared; 95 mL of the prepared nickel salt solution was impregnated into 100 g of the $Al_2O_3$ carrier, stood for 80 mins, then dried for 12 hours at a temperature raised to 120° C., and calcined for 5 hours at a constant temperature of 400° C. raised at 2° C./min in an air atmosphere to obtain a $NiO/Al_2O_3$ precursor having a mass ratio of $Al_2O_3$:Ni to be 100:9.5.

The ethanol-water solution of aluminum precursor and silicon precursor with a concentration of 0.0008 g/mL by calculating $Al_2O_3$—$SiO_2$ was prepared from aluminum isopropoxide and TEOS with a molar ratio of Al:Si to be 0.05:1, a molar ratio of ethanol to water in the ethanol-water solution was 20:1, and a pH value of the ethanol-water solution was adjusted to be 8.4 by ammonia water. The $NiO/Al_2O_3$ precursor prepared with the mass ratio of $Al_2O_3$:Ni to be 100:9.5 was suspended in 1300 mL of ethanol-water solution of aluminum precursor and silicon precursor, stirred and refluxed for 24 hours at a constant temperature of 20° C., centrifugal washed three times respectively with absolute ethyl alcohol, 0.01M dilute nitric acid and deionized water after filtration, and the sample was dried for 12 hours at 100° C. The obtained sample was placed in a muffle furnace to calcine for 1 hour at a constant temperature of 400° C. raised at 10° C./min in a nitrogen atmosphere, and then reduction was conducted for 24 hours at 450° C. under the condition of a gas space velocity of hydrogen of 1500/h to obtain a Ni—$Al_2O_3$@$Al_2O_3$—$SiO_2$ catalyst with a quality composition of $Al_2O_3$:$Al_2O_3$—$SiO_2$:Ni=100:1.04:9.5, wherein a molar ratio of Al:Si in the $Al_2O_3$—$SiO_2$ layer was 0.05:1. The catalyst had a specific surface area of 145 m²/g, and a pore volume of 0.61 cm³/g, Ni particles were distributed on a surface of the $Al_2O_3$ carrier in a highly dispersed state and had a grain size of 6.3 nm, and the $Al_2O_3$—$SiO_2$ layer formed Al—O—Si bonds that filled among the Ni particles. The catalyst was numbered as 4 #.

EXAMPLE 5

The $Al_2O_3$ carrier having a specific surface area of 210 m²/g, and a pore volume of 1.0 cm³/g was heated for 5 hours at 130° C. in an air-circulating oven, and then cooled to a room temperature for use; a nickel salt solution of nickel nitrate having a nickel content of 0.15 g/mL was prepared; 110 mL of the prepared nickel salt solution was impregnated into 100 g of the $Al_2O_3$ carrier, stood for 20 mins, then dried for 3 hours at a temperature raised to 100° C., and calcined for 1 hour at a constant temperature of 500° C. raised at 10° C./min in an air atmosphere to obtain a $NiO/Al_2O_3$ precursor having a mass ratio of $Al_2O_3$:Ni to be 100:16.5.

The ethanol-water solution of aluminum precursor and silicon precursor with a concentration of 0.0012 g/mL by calculating $Al_2O_3$—$SiO_2$ was prepared from aluminum n-butanol and TEOS with a molar ratio of Al:Si to be 0.07:1, a molar ratio of ethanol to water in the ethanol-water solution was 4:1, and a pH value of the ethanol-water solution was adjusted to be 8.0 by ammonia water. The $NiO/Al_2O_3$ precursor prepared with the mass ratio of $Al_2O_3$:Ni to be 100:16.5 was suspended in 1700 mL of ethanol-water solution of aluminum precursor and silicon precursor, stirred and refluxed for 24 hours at a constant temperature of 20° C., centrifugal washed five times respectively with absolute ethyl alcohol, 0.01M dilute nitric acid and deionized water after filtration, and the sample was dried for 3 hours at 80° C. The obtained sample was placed in a muffle furnace to calcine for 1 hour at a constant temperature of 400° C. raised at 2° C./min in an air atmosphere, and then reduction was conducted for 1 hour at 350° C. under the condition of a gas space velocity of hydrogen of 1500/h to obtain a Ni—$Al_2O_3$@$Al_2O_3$—$SiO_2$ catalyst with a quality composition of $Al_2O_3$:$Al_2O_3$—$SiO_2$:Ni=100:2.04:16.5, wherein a molar ratio of Al:Si in the $Al_2O_3$—$SiO_2$ layer was 0.07:1. The catalyst had a specific surface area of 183 m²/g, and a pore volume of 0.85 cm³/g, Ni particles were distributed on a surface of the $Al_2O_3$ carrier in a highly dispersed state and had a grain size of 7.5 nm, and the $Al_2O_3$—$SiO_2$ layer formed Al—O—Si bonds that filled among the Ni particles. The catalyst was numbered as 5 #.

Figure 2:
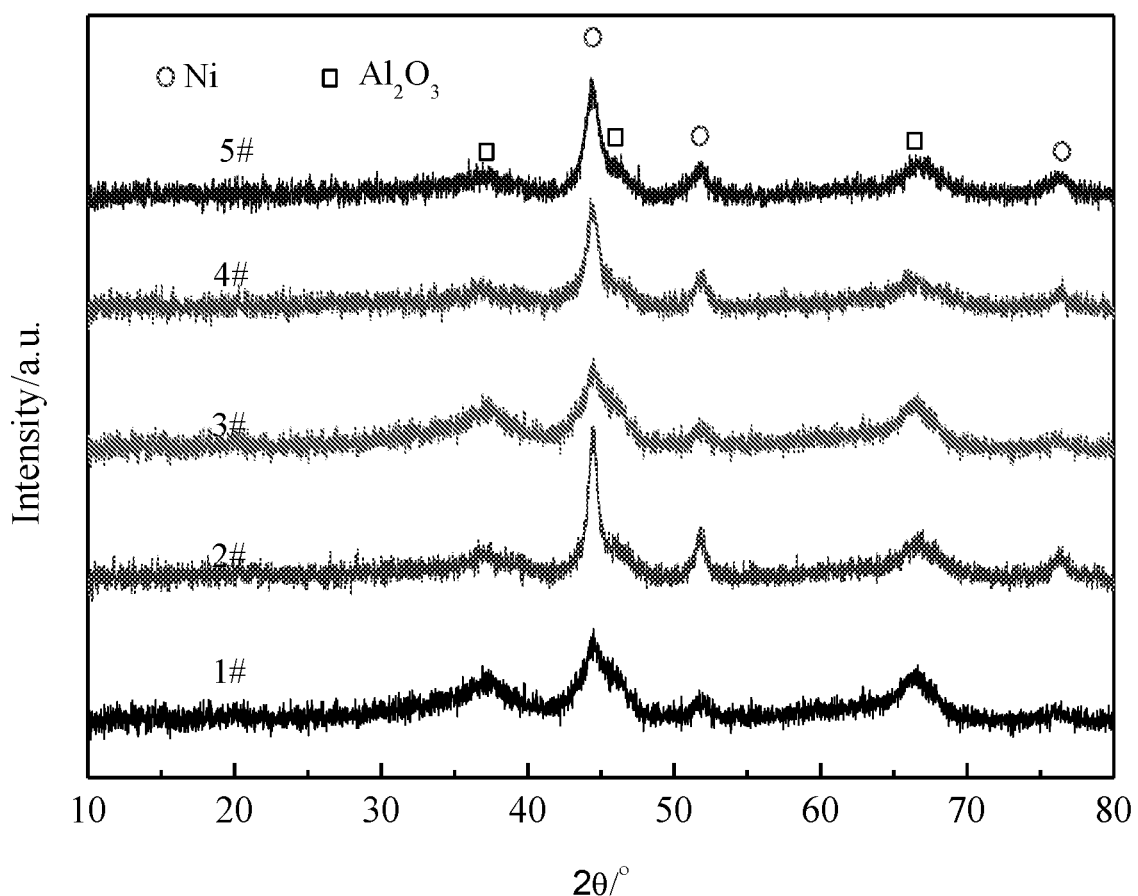
FIG. 2 is an XRD diagram of the catalyst according to the invention.
Figure 3:
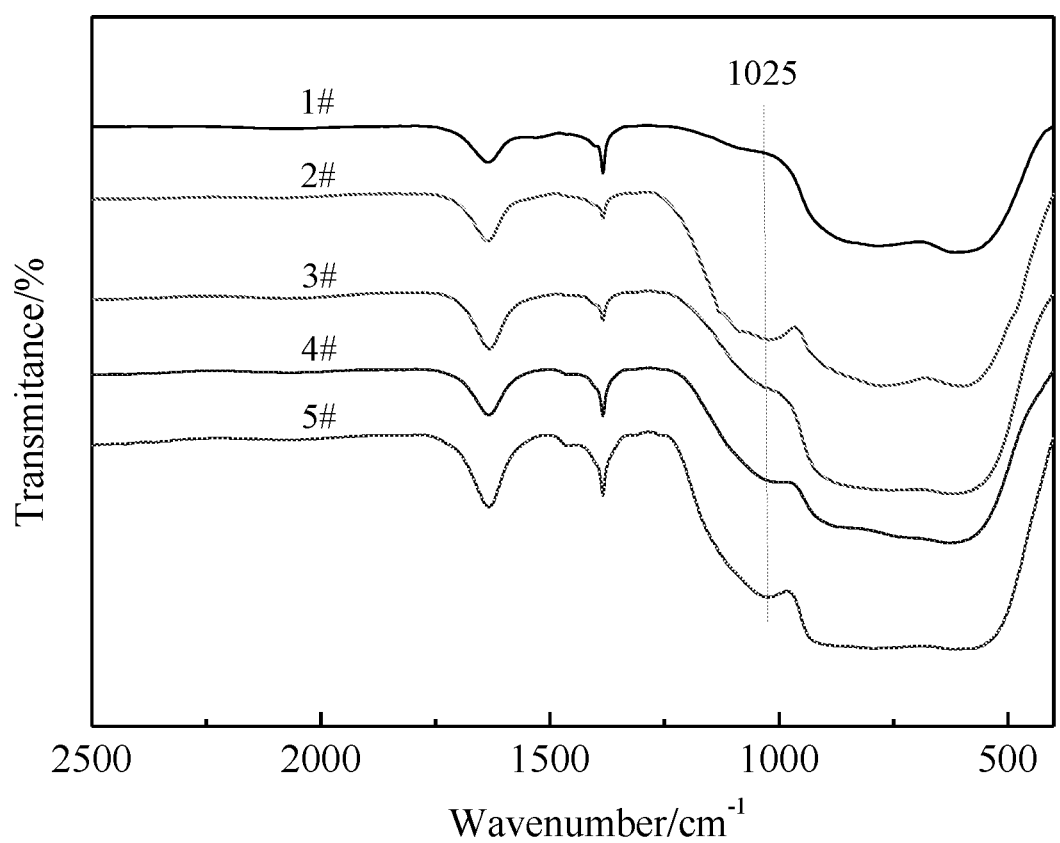
FIG. 3 is a FT-IR diagram of the catalyst according to the invention.

Catalyst structures of the catalysts 1 #-5 # are characterized by XRD, IR and XPS techniques. XRD diagrams of the reduced catalysts are illustrated in FIG. 2. All catalysts exhibit dispersed characteristic diffraction peaks of γ-$Al_2O_3$ at 2θ=37°, 46° and 66.5°, and exhibit characteristic peaks of the metal Ni at 2θ=44. 5°, 51. 7° and 76. 4°. Ni grain sizes are calculated by the formula Scherrer using a half-width of the Ni (200) crystal plane diffraction peak at 2θ=51. 7°, which are listed in Table 1. As can be seen, Ni particles are highly dispersed, and the grain sizes are below 8 nm. FT-IR diagrams of respective catalysts are illustrated in FIG. 3. As can be seen, a new infrared absorption peak appears at 1024 cm$^{-1}$, which belongs to a vibration absorption peak of the Si—O—Al bonds. This result shows that the loaded $SiO_2$ is bonded with $Al_2O_3$ to form new Si—O—Al bonds. After further XPS analysis on the catalysts, atomic ratios of Ni/(Al+Si) on surfaces of the catalysts 1 #-5 # are calculated in accordance with XPS data. In order to make comparison, atomic ratios of Ni/Al in the $Ni/Al_2O_3$ catalyst when the $SiO_2$—$Al_2O_3$ layer is not loaded are also calculated, and results are listed in Table 1. As can be seen, the atomic ratios of Ni/Al before loading the $SiO_2$—$Al_2O_3$ layer onto the catalyst are in close proximity to the atomic ratios of Ni/(Al+Si) after loading the $SiO_2$—$Al_2O_3$ layer, and it is further determined that the loaded $SiO_2$—$Al_2O_3$ layer is selectively deposited on the $Al_2O_3$ surface to form the Si—O—Al bonds and form the coating structure shown in FIG. 1.

TABLE 1

Ni Grain Size and Ni Surface Concentration

| No. | Average Ni Grain Size | Ratio of Ni/ (Si + Al) | Ratio of Ni/Al of the Sample Before Loading $Al_2O_3$—$SiO_2$ |
|---|---|---|---|
| 1# | — | 0.041 | 0.042 |
| 2# | 8 | 0.69 | 0.71 |
| 3# | — | 0.042 | 0.043 |
| 4# | 6.3 | 0.18 | 0.19 |
| 5# | 7.5 | 0.50 | 0.51 |

EXAMPLE 6

The catalyst was for hydrogenation of 1,4-butynediol under a high pressure to catalytic synthesize butane-1,4-diol, wherein a raw material contained 64 wt % to 72 wt % water, an organic phase contained 90 wt % to 91.5 wt % butane-1,4-diol, 1 wt % to 2 wt % butanol, 1.3 wt % to 1.8 wt % 4-hydroxybutyraldehyde, 1.5 wt % to 2 wt % 1,4-butynediol, 2.7 wt % to 3.2 wt % 1,4-butenediol, and 0.8 wt % to 1.2 wt % cyclic acetal, 2-(4'-hydroxybutoxy)-tetrahydrofuran, the carbonyl number was 8 mg(KOH)/g to 12 mg(KOH)/g, and hydrogenation was conducted under the conditions of a reaction temperature of 100° C. to 150° C., a pressure of 10 MPa to 20 MPa, and a liquid hourly space velocity of 1.1/h to 1.7/h. After hydrogenation, an organic phase contained 96.44 wt % to 97.76 wt % butane-1,4-diol, 1.3 wt % to 2.5 wt % butanol, 0.03 wt % to 0.08 wt % 4-hydroxybutyraldehyde, 0.01 wt % to 0.05 wt % 1,4-butynediol, 0.03 wt % to 0.07 wt % 1,4-butenediol, and 0.01 wt % to 0.03 wt % cyclic acetal, 2-(4'-hydroxybutoxy)-tetrahydrofuran, and the carbonyl number was 0.03 mg(KOH)/g to 0.05 mg(KOH)/g. Compositions of raw materials for evaluation of respective catalysts are shown in Table 2, catalytic hydrogenation reaction conditions are shown in Table 3, and compositions of materials for evaluation after hydrogenation of respective catalysts are shown in Table 4.

TABLE 2

Compositions of Raw Materials for Evaluation of Respective Catalysts

| No. of Catalysts | Water % | butane-1,4-diol/ wt % | Butanol/ wt % | 4-hydroxybutyraldehyde/ wt % | 1,4-butynediol/ wt % | 1,4-butenediol/ wt % | Acetal/ wt % | Other/ wt % | Carbonyl number/ mg (KOH) · g$^{-1}$ |
|---|---|---|---|---|---|---|---|---|---|
| 1# | 64 | 91.1 | 1.5 | 1.7 | 1.5 | 2.9 | 0.8 | 0.5 | 9.3 |
| 2# | 72 | 90   | 1.2 | 1.8 | 2   | 3.1 | 1.1 | 0.8 | 12 |
| 3# | 66 | 90.2 | 2   | 1.3 | 1.7 | 3.2 | 1.0 | 0.6 | 8 |
| 4# | 70 | 91.5 | 1   | 1.5 | 1.6 | 2.7 | 1.2 | 0.5 | 10.7 |
| 5# | 68 | 90.4 | 1.7 | 1.6 | 1.9 | 2.8 | 0.9 | 0.7 | 9.3 |

TABLE 3

Catalytic Hydrogenation Reaction Conditions

| No. of Catalysts | Temperature/° C. | Pressure/MPa | Liquid hourly space velocity/h |
|---|---|---|---|
| 1# | 110 | 15 | 1.1 |
| 2# | 140 | 10 | 1.5 |
| 3# | 150 | 17 | 1.7 |
| 4# | 100 | 20 | 1.3 |
| 5# | 125 | 13 | 1.2 |

TABLE 4

Compositions of Materials for Evaluation After Hydrogenation of Respective Catalysts

| No. of Catalysts | Water % | butane-1,4-diol/ wt % | Butanol/ wt % | 4-hydroxybutyraldehyde/ wt % | 1,4-butynediol/ wt % | 1,4-butenediol/ wt % | Acetal/ wt % | Other/ wt % | Carbonyl number/ mg (KOH) · g$^{-1}$ |
|---|---|---|---|---|---|---|---|---|---|
| 1# | 64 | 97.26 | 1.8 | 0.06 | 0.02 | 0.05 | 0.01 | 0.8  | 0.03 |
| 2# | 72 | 97.44 | 1.5 | 0.08 | 0.05 | 0.07 | 0.02 | 0.84 | 0.05 |
| 3# | 66 | 96.64 | 2.5 | 0.03 | 0.04 | 0.07 | 0.02 | 0.7  | 0.05 |
| 4# | 70 | 97.76 | 1.3 | 0.07 | 0.01 | 0.03 | 0.03 | 0.8  | 0.03 |
| 5# | 68 | 96.67 | 2.2 | 0.05 | 0.02 | 0.05 | 0.01 | 1.0  | 0.04 |

EXAMPLE 7

The catalysts 1 #-5 #were selected with a water solution containing 25 wt % to 35 wt % 1,4-butynediol as the raw material using an external cyclic hydrogenation process, wherein a way of feeding was up-in and down-out, and reaction conditions were a reaction temperature of 105° C. to 150° C., a hydrogen pressure of 10 MPa to 22 MPa, a liquid hourly space velocity of 1.0/h to 1.7/h, and a recycle ratio of 18~22:1. After hydrogenation, the organic phase of the material contained butane-1,4-diol greater than or equal to 96 wt %, by-product butanol less than or equal to 1.2 wt %, and a total unsaturated chromogenic substance of 1,4-butynediol, 1,4-butenediol, 4-hydroxybutyraldehyde, hemiacetal and acetal, 2-(4'-hydroxybutoxy)-tetrahydrofuran less than or equal to 0.06 wt %, the remaining was macromolecular polymer, and the carbonyl number of the material was 0.03 mg(KOH)/g to 0.05 mg(KOH)/g. Specific reaction conditions and results are shown in Table 5.

TABLE 5

Reaction Conditions and Compositions of Material After Hydrogenation

| | Raw Material | Reaction Conditions | | | | Compositions of Organic Phase of Hydrogenated Material | | | | |
|---|---|---|---|---|---|---|---|---|---|---|
| No. | Index 1,4-butynediol/ wt % | Temperature/ ° C. | Pressure/ MPa | Liquid hourly space velocity/h | Recycle Ratio | butane-1,4-diol/ wt % | Butanol/ wt % | Unsaturated Chromogenic Substance/ wt % | Other/ wt % | Carbonyl number/ mg (KOH)/g |
| 1# | 28 | 135 | 13 | 1.2 | 19:1 | 98.11 | 0.6 | 0.04 | 1.25 | 0.03 |
| 2# | 32 | 110 | 22 | 1.3 | 18:1 | 96.16 | 1.2 | 0.05 | 2.59 | 0.03 |
| 3# | 30 | 150 | 17 | 1.5 | 22:1 | 97 | 0.8 | 0.06 | 2.14 | 0.05 |
| 4# | 35 | 120 | 10 | 1.7 | 20:1 | 97.41 | 1.0 | 0.05 | 1.54 | 0.04 |
| 5# | 25 | 105 | 15 | 1.0 | 18:1 | 96.85 | 0.7 | 0.03 | 2.42 | 0.05 |

INDUSTRIAL APPLICABILITY

The Al—O—Si structure formed by the $Al_2O_3$—$SiO_2$ layer in the catalyst of the invention enables it to have a specific surface acidic property, which may facilitate hydrolyzation of cyclic acetal, 2-(4'-hydroxybutoxy)-tetrahydrofuran to 4-hydroxybutyraldehyde, and then hydrogenation conversion to butane-1,4-diol under catalysis of adjacent high activity exposed hydrogenation center Ni. Synergistic effect of the acidic center and the hydrogenation active center in the catalyst achieves efficient conversion of cyclic acetal, 2-(4'-hydroxybutoxy)-tetrahydrofuran, and finally reaches objects of reducing the content of cyclic acetal, 2-(4'-hydroxybutoxy)-tetrahydrofuran, improving product quality of butane-1,4-diol, and reducing product chromaticity.

The organic phase of the material after hydrogenation contains butane-1,4-diol greater than or equal to 96 wt %, by-product butanol less than or equal to 1.2 wt %, and a total unsaturated chromogenic substance of 1,4-butynediol, 1,4-butenediol, 4-hydroxybutyraldehyde, hemiacetal and acetal, 2-(4'-hydroxybutoxy)-tetrahydrofuran less than or equal to 0.06 wt %, the remaining is macromolecular polymer, and the carbonyl number of the material is 0.03 mg(KOH)/g to 0.05 mg(KOH)/g.

Of course, the invention also may have many other examples, and those persons skilled in the art may make various corresponding modifications and variations according to the invention without departing from spirit and substance of the invention, but these corresponding modifications and variations shall belong to the extent of protection of the claims in the invention.

What is claimed is:

1. A Ni—$Al_2O_3$@$Al_2O_3$—$SiO_2$ catalyst with coated structure, comprising: Ni particles distributed on a surface of an $Al_2O_3$ carrier in an amorphous or highly dispersed state as an active component for the catalyst, and the Ni particles have a grain size less than or equal to 8 nm, and an $Al_2O_3$—$SiO_2$ coating layer, wherein a mass ratio of the $Al_2O_3$ carrier to the $Al_2O_3$—$SiO_2$ coating layer is $Al_2O_3$:$Al_2O_3$—$SiO_2$=100:0.1~3, a molar ratio of Al to Si in the $Al_2O_3$—$SiO_2$ coating layer is 0.01~0.1:1, and the coating layer is filled among the Ni particles.

2. The Ni—$Al_2O_3$@$Al_2O_3$—$SiO_2$ catalyst with coated structure according to claim 1, wherein the catalyst has a specific surface area of 98 $m^2$/g ~245 $m^2$/g, and a pore volume of 0.25 $cm^3$/g~1.1 $cm^3$/g, and a mass ratio of the $Al_2O_3$ carrier to the active component Ni in the catalyst is $Al_2O_3$: Ni=100:4~26.

3. A preparation method of the Ni—$Al_2O_3$@$Al_2O_3$—$SiO_2$ catalyst with coated structure according to claim 1, comprising the steps of:
    impregnation step: loading the active component Ni onto the $Al_2O_3$ carrier using an impregnation method, Ni being distributed in tetrahedral and octahedral holes on an $Al_2O_3$ surface and growing into microcrystalline particles by using the tetrahedral and octahedral holes as nuclei;
    deposition step: loading the $Al_2O_3$—$SiO_2$ layer in a depositing manner onto a surface of a Ni/$Al_2O_3$ catalyst obtained in the impregnation step, $Al_2O_3$—$SiO_2$ only deposited on the $Al_2O_3$ surface exposed in gaps of the Ni particles; and
    washing step: removing weak adsorption compositions remaining on the surface of the catalyst by washing the deposited sample.

4. A preparation method of the Ni—$Al_2O_3$@$Al_2O_3$—$SiO_2$ catalyst with coated structure according to claim 1, comprising the steps of:
    (1) cooling the $Al_2O_3$ carrier to a room temperature for use after treatment at 100° C. to 150° C.;
    (2) preparing a nickel salt water solution having a nickel content of 0.05 g/mL to 0.2 g/mL;
    (3) impregnating the nickel salt water solution prepared by step (2) into the carrier of step (1) according to a ratio of 80 mL to 130 mL of nickel salt solution for 100 g of the $Al_2O_3$ carrier, standing, drying and calcining to obtain a NiO/$Al_2O_3$ precursor;
    (4) preparing an ethanol-water solution of aluminum precursor and silicon precursor with a total concentration of 0.0001 g/mL to 0.0015 g/mL by calculating $Al_2O_3$ and $SiO_2$, and adjusting a pH value of the ethanol-water solution to 8.0 to 8.5 by ammonia water, wherein a molar ratio of Al to Si is 0.01~0.1:1;

(5) suspending the $NiO/Al_2O_3$ precursor obtained by step (3) in the solution prepared by step (4) according to an amount of 1000 mL to 2000 mL of ethanol-water solution of aluminum precursor and silicon precursor for 100 g of $Al_2O_3$ in the $NiO/Al_2O_3$ precursor of step (3), stirring and refluxing at a constant temperature, centrifugal washing respectively with absolute ethyl alcohol, dilute nitric acid and deionized water after filtration, and drying; and (6) calcining the sample obtained by step (5), then conducting hydrogen reduction to obtain a $Ni-Al_2O_3@Al_2O_3-SiO_2$ catalyst.

5. A preparation method of the $Ni-Al_2O_3@Al_2O_3-SiO_2$ catalyst with coated structure according to claim 1, comprising the steps of:

(1) vacuum treating the $Al_2O_3$ carrier for 10 mins to 30 mins at 100° C. to 150° C., or directly heating for 1 hour to 10 hours at 100° C. to 150° C., and then cooling to a room temperature for use;

(2) preparing a nickel salt solution having a nickel content of 0.05 g/mL to 0.2 g/mL;

(3) impregnating the nickel salt solution prepared by step (2) into the carrier of step (1) according to a ratio of 80 mL to 130 mL of nickel salt solution for 100 g of the $Al_2O_3$ carrier, standing for 20 mins to 120 mins, then drying for 2 hours to 24 hours at a temperature raised to 100° C. to 150° C., and calcining for 1 hour to 24 hours at a constant temperature of 350° C. to 500° C. raised at 2° C./min to 10° C./min in an air or nitrogen atmosphere to obtain a $NiO/Al_2O_3$ precursor;

(4) preparing an ethanol-water solution of aluminum precursor and silicon precursor with a total concentration of 0.0001 g/mL to 0.0015 g/mL by calculating $Al_2O_3$ and $SiO_2$, and adjusting a pH value of the ethanol-water solution to 8.0 to 8.5 by ammonia water, wherein a molar ratio of Al to Si is 0.01~0.1:1;

(5) suspending the $NiO/Al_2O_3$ precursor obtained by step (3) in the solution prepared by step (4) according to an amount of 1000 mL to 2000 mL of ethanol-water solution of aluminum precursor and silicon precursor for 100 g of $Al_2O_3$ in the $NiO/Al_2O_3$ precursor of step (3), stirring and refluxing for 1 hour to 24 hours at a constant temperature of 20° C. to 60° C., centrifugal washing three to five times respectively with absolute ethyl alcohol, 0.01 M dilute nitric acid and deionized water after filtration, and drying the sample for 2 hours to 24 hours at 80° C. to 150° C.; and (6) calcining the sample obtained by step (5) for 1 hour to 24 hours at a constant temperature of 400° C. to 550° C. raised at 2° C./min to 10° C./min in an air or nitrogen atmosphere, and then conducting reduction for 1 hour to 24 hours at 350° C. to 650° C. under the condition of a gas space velocity of hydrogen of 500/h to 2000/h to obtain a $Ni-Al_2O_3@Al_2O_3-SiO_2$ catalyst.

6. The preparation method of the $Ni-Al_2O_3@Al_2O_3-SiO_2$ catalyst with coated structure according to claim 5, wherein the $Al_2O_3$ carrier in step (1) has a specific surface area of 110 $m^2/g$ to 260 $m^2/g$, and a pore volume of 0.5 $cm^3/g$ to 1.3 $cm^3/g$.

7. The preparation method of the $Ni-Al_2O_3@Al_2O_3-SiO_2$ catalyst with coated structure according to claim 5, wherein the nickel salt in the nickel salt solution of step (2) is one of a nickel nitrate, a nickel sulfate or a nickel chloride.

8. The preparation method of the $Ni-Al_2O_3@Al_2O_3-SiO_2$ catalyst with coated structure according to claim 5, wherein a drying time in step (3) is 3 hours to 12 hours.

9. The preparation method of the $Ni-Al_2O_3@Al_2O_3-SiO_2$ catalyst with coated structure according to claim 5, wherein the silicon precursor in step (3) is one of tetraethoxysilane (TEOS), or tetramethoxysilane (TMOS).

10. The preparation method of the $Ni-Al_2O_3@Al_2O_3-SiO_2$ catalyst with coated structure according to claim 9, wherein the silicon precursor is TEOS.

11. The preparation method of the $Ni-Al_2O_3@Al_2O_3-SiO_2$ catalyst with coated structure according to claim 5, wherein the aluminum precursor in step (3) is one of aluminum isopropoxide, aluminum n-butanol, or aluminum nitrate.

12. The preparation method of the $Ni-Al_2O_3@Al_2O_3-SiO_2$ catalyst with coated structure according to claim 11, wherein the aluminum precursor is aluminum nitrate.

13. The preparation method of the $Ni-Al_2O_3@Al_2O_3-SiO_2$ catalyst with coated structure according to claim 5, wherein a molar ratio of ethanol to water in the ethanol-water solution of step (4) is 4~100:1.

14. The preparation method of the $Ni-Al_2O_3@Al_2O_3-SiO_2$ catalyst with coated structure according to claim 5, wherein a drying time in step (5) is 3 hours to 12 hours.

15. An application of the $Ni-Al_2O_3@Al_2O_3-SiO_2$ catalyst with coated structure according to claim 1, wherein the catalyst is for hydrogenation of 1,4-butynediol to catalytically synthesize butane-1,4-diol.

16. The application of the $Ni-Al_2O_3@Al_2O_3-SiO_2$ catalyst with coated structure according to claim 15, comprising the step of:

Hydrogenation of 1,4-butynediol under a high pressure to catalytic synthesize butane-1,4-diol, wherein a raw material contains 64 wt % to 72 wt % water, an organic phase contains 90 wt % to 91.5 wt % butane-1,4-diol, 1 wt % to 2 wt % butanol, 1.3 wt % to 1.8 wt % 4-hydroxybutyraldehyde, 1.5 wt % to 2 wt % 1,4-butynediol, 2.7 wt % to 3.2 wt % 1,4-butenediol, and 0.8 wt % to 1.2 wt % cyclic acetal, 2-(4'-hydroxybutoxy)-tetrahydrofuran, the carbonyl number is 8 mg(KOH)/g to 12 mg(KOH)/g, and hydrogenation is conducted under the conditions of a reaction temperature of 100° C. to 150° C., a hydrogen pressure of 10 MPa to 20 MPa, and a liquid hourly space velocity of 1.1/h to 1.7/h to produce an organic phase product.

17. The application of the $Ni-Al_2O_3@Al_2O_3-SiO_2$ catalyst with coated structure according to claim 16, wherein the organic phase product after hydrogenation contains 96.44 wt % to 97.76 wt % butane-1,4-diol, 1.3 wt % to 2.5 wt % butanol, 0.03 wt % to 0.08 wt % 4-hydroxybutyraldehyde, 0.01 wt % to 0.05 wt % 1,4-butynediol, 0.03 wt % to 0.07 wt % 1,4-butenediol, and 0.01 wt % to 0.03 wt % cyclic acetal, 2-(4'-hydroxybutoxy)-tetrahydrofuran, and the carbonyl number is 0.03 mg(KOH)/g to 0.05 mg(KOH)/g.

18. The application of the $Ni-Al_2O_3@Al_2O_3-SiO_2$ catalyst with coated structure according to claim 15, comprising the step of:

Direct hydrogenation conversion of a raw material which is a water solution containing 25 wt % to 35 wt % 1,4-butynediol using an external cyclic hydrogenation process, wherein a way of feeding is up-in and down-out, and reaction conditions are a reaction temperature of 105° C. to 150° C., a hydrogen pressure of 10 MPa to 22 MPa, a liquid hourly space velocity of 1.0/h to 1.7/h, and a recycle ratio of 18 22:1 to produce an organic phase product.

19. The application of the Ni—$Al_2O_3$@$Al_2O_3$—$SiO_2$ catalyst with coated structure according to claim 18, wherein the organic phase product of the material after hydrogenation contains butane-1,4-diol greater than or equal to 96 wt %, by-product butanol less than or equal to 1.2 wt %, and a total unsaturated chromogenic substance less than or equal to 0.06 wt %, the remaining is macromolecular polymer, and the carbonyl number of the material is 0.03 mg(KOH)/g to 0.05 mg(KOH)/g.

\* \* \* \* \*